(12) United States Patent
Schmidt et al.

(10) Patent No.: US 8,236,863 B2
(45) Date of Patent: Aug. 7, 2012

(54) SALINE SOLUTIONS FOR CLINICAL OR COSMETIC USE

(75) Inventors: Ryszard Jan Schmidt, Barnoldswick (GB); James Martin Biggs, Godalming (GB)

(73) Assignee: Pharma Sol International Limited, Goldalming, Surrey (GB)

( * ) Notice: Subject to any disclaimer, the term of this patent is extended or adjusted under 35 U.S.C. 154(b) by 1092 days.

(21) Appl. No.: 10/490,811

(22) PCT Filed: Sep. 26, 2002

(86) PCT No.: PCT/GB02/04387
§ 371 (c)(1), (2), (4) Date: Sep. 27, 2004

(87) PCT Pub. No.: WO03/026679
PCT Pub. Date: Apr. 3, 2003

(65) Prior Publication Data
US 2005/0031707 A1 Feb. 10, 2005

(30) Foreign Application Priority Data
Sep. 26, 2001 (GB) .................... 0123115.8

(51) Int. Cl.
*A61K 47/00* (2006.01)
(52) U.S. Cl. .................... 514/769; 514/887
(58) Field of Classification Search ............ 514/769, 514/886
See application file for complete search history.

(56) References Cited

U.S. PATENT DOCUMENTS

| | | | | |
|---|---|---|---|---|
| 3,551,290 | A | * 12/1970 | Kuwahara et al. | 435/1.1 |
| 4,550,022 | A | 10/1985 | Garabedian et al. | |
| 5,281,353 | A | * 1/1994 | Park et al. | 510/114 |
| 5,488,069 | A | * 1/1996 | Stroppolo et al. | 514/772.4 |
| 5,514,536 | A | 5/1996 | Taylor | |
| 5,811,446 | A | * 9/1998 | Thomas | 514/399 |
| 5,861,148 | A | * 1/1999 | Smith | 424/78.04 |
| 5,945,272 | A | 8/1999 | Segall et al. | |
| 6,121,250 | A | * 9/2000 | Nishiyama et al. | 514/57 |

(Continued)

FOREIGN PATENT DOCUMENTS

GB 2308810 A 7/1997

(Continued)

OTHER PUBLICATIONS

Zavadiak, Lavage of the digestive tract with an isotonic mineral water-based 3-salt solution, 1999, Lik Sprava, (5), printed from http://www.ncbi.nlm.nih.gov/sites/entrez on Jan. 21, 2009, Abstract only, 2 pages.*

(Continued)

*Primary Examiner* — Sreeni Padmanabhan
*Assistant Examiner* — Gigi Huang
(74) *Attorney, Agent, or Firm* — Jenkins, Wilson, Taylor & Hunt, P.A.

(57) ABSTRACT

A saline solution for a clinical or cosmetic use which consists essentially of a solution in water of sodium ions in major amount and potassium ions in minor amount, together with physiologically acceptable counter ions, being isotonic or optionally slightly hypertonic or hypotonic with respect to blood plasma or tears or an otherwise relevant biological fluid, and being substantially free of calcium ions, magnesium ions, phosphate ions, bicarbonate ions and also glucose, sucrose, food starch or other glucose-releasing saccharides, for use as a more cell-friendly alternative to normal saline.

5 Claims, 3 Drawing Sheets

U.S. PATENT DOCUMENTS

| | | | |
|---|---|---|---|
| 6,271,216 | B1 | 8/2001 | Mello et al. |
| 6,277,365 | B1* | 8/2001 | Ellis et al. ............... 424/78.04 |

FOREIGN PATENT DOCUMENTS

| | | |
|---|---|---|
| JP | EP 0778021 A1 | 6/1997 |
| WO | WO 01/47576 A2 | 7/2001 |
| WO | WO 03/026679 A2 | 4/2003 |

OTHER PUBLICATIONS

Illinois Deparment of Public Health, Commonly Found Substances in Drinking Water, 2002, printed from http://web.archive.org/web/20020916123901/http://www.idph.state.il.us/envhealth/pdf/DrinkingWater.pdf, 9 pages.*

The Coca-Cola Company, 2009, Ensuring Quality in the DASANI (R) Manufacturing Process-Mineralization of Water, printed from http://www.thecoca-colacompany.com/flash/csr/dasani/index.html, 2 pages.*

The Coca-Cola Company, 2009, Ensuring Quality in the DASANI (R) Manufacturing Process-Water purification, printed from http://www.thecoca-colacompany.com/flash/csr/dasani/index.html, 1 page.* www.Danasi.com, 2001, Frequently asked questions, printed from http://web.archive.org/web/20010124012800/http://dasani.com/, 2 pages.*

Baxter, Potassium Chloride in Sodium Chloride (0.9%) Intravenous Infusion BP, 2000, Baxter, package insert printed from http://www.oceania.baxter.com/downloads/products/cmi/potassium_chloride_in_sodium_chloride.pdf on Sep. 9, 2009, 3 pages.*

Drugs.com, Potassium Chloride in Sodium Chloride, printed from http://www.drugs.com/pro/potassium-chloride-in-sodium-chloride.html?printable=1 on Jul. 2, 2010, 10 pages.*

CNA Medical, Baxter Colleague IV Pump, Feb. 1, 2001, printed from http://www.cnamedical.com/baxter_colleague.htm, Google date page of entry to the internet included, 3 pages.*

Cardinal Health, IV Solutions, Feb. 1, 2001, printed from http://www.cardinal.com/us/en/distributedproducts/index.asp?ID=Medical%20and%20Surgical%20Products;IV%20Solutions;&cat=med_surg, Google date page of internet entry included, 2 pages.*

Monograph for compound sodium chloride injection, *British Pharmaceutical Codex 1959*, London: Pharmaceutical Press, pp. 685-687.

Ringer's Irrigation, *United States Pharmacopoeia (USP 23)* 1995. Rockville, MD: United States Pharmacopeia Convention, 1994, pp. 1389, 1383-1384.

Isotonic and Isosmotic Solutions, *Pharmaceutical Handbook, 18th Edition*. London: Pharmaceutical Press, 1970, pp. 219-224.

Sodium Chloride Office, *British Pharmacopoeia 2001*, vol. 1. London: The Stationery Office, pp. 1481-1482.

Sodium Chloride Irrigation, *United States Pharmacopoeia (USP 23)* 1995. Rockville, MD: United States Pharmacopoeia Convention, 1994, pp. 1418-1419.

Acland et al., "Irrigating Solutions for Small Blood Vessel Surgery—A Histologic Comparison", *Plastic and Reconstructive Surgery*, vol. 65, No. 4, pp. 460-465, Apr. 1980.

Angerås et al., "Comparison Between Sterile Saline and Tap Water for the Cleaning of Acute Traumatic Soft Tissue Wounds," *Eur J Surg*, vol. 158, pp. 347-350, 1992.

Brennan et al., "Antiseptic toxicity in wounds healing by secondary intention," *Journal of Hospital Infection* vol. 8, pp. 263-267, 1986.

Cooper et al., "The Cytotoxic Effects of Commonly Used Topical Antimicrobial Agents on Human Fibroblasts and Keratinocytes," *The Journal of Trauma*, vol. 31, No. 6, pp. 775-784, Jun. 1991.

Foresman et al., "A Relative Toxicity Index for Wound Cleansers," *WOUNDS: A Compendium of Clinical Research and Practice*, vol. 5, No. 5, pp. 226-231, Sep./Oct. 1993.

Hansen et al., "Re-examination and further development of a precise and rapid dye method for measuring cell growth/cell kill," *Journal of Immunological Methods*, vol. 119, pp. 203-210, 1989.

Heimbürger et al., "Physiological saline is not a biocompatible peritoneal dialysis solution," *The Intl J of Artificial Organs*, vol. 22, No. 2, pp. 88-93, 1999.

Hellewell et al., "A Cytotoxicity Evaluation of Antimicrobial and Non-Antimicrobial Wound Cleansers," *Wounds*, vol. 9, No. 1, pp. 15-20, Jan./Feb. 1997.

Jay et al., "Effects of intraocular miotics on cultured bovine corneal endothelium," *British Journal of Opthalmology*, vol. 62, pp. 815-820, 1978.

Martindale WH & Westcott WW., "Saline Solution, Normal." *The Extra Pharmacopoeia*, 16th Ed. London: HK Lewis & Company, 1915, p. 722.

Moscati et al., "Comparison of Normal Saline with Tap Water for Wound Irrigation," *American Journal of Emergency Medicine*, vol. 16, No. 4, pp. 379-381, Jul. 1998.

Moscati et al., "Wound Irrigation with Tap Water," *Academic Emergency Medicine*, vol. 5, No. 11, pp. 1076-1080, Nov. 1998.

Todd RG (Ed.) "Isotonic and Isosmotic Solutions," *Pharmaceutical Handbook*, 18th Ed. London: Pharmaceutical Press, 1970, pp. 219-221.

International Search Report corresponding to International Patent Application No. PCT/GB2002/004387 dated May 2, 2003.

"Improving of health," <http://www.jivavoda.com.ua/documents/ozdorov.html> (Accessed on Sep. 22, 2011) (2 pages).

"Mineral Waters of the World," www.mineralwaters.org <http://www.mineralwaters.org/index.php?func=disp&parval=1609> (Accessed on Sep. 22, 2011) (1 page).

"Polyana Kupel," <http://www.alex.com.ua/En/kupel.html> (Accessed on Sep. 22, 2011) (2 pages).

"Shayan, Sanatoriums (Carpathians (Zakarpattia))," Hotel Shayan, Sanatorium in Carpathians (Zakarpattia) website. <http://idriska-tour.com/en/hotel/2989/shayan-sanatorium.html> (Accessed on Sep. 22, 2011) (3 pages).

"The mineral water <<Polyana Kvasova>>," Resort house, Sonyachna Dolyna, Transcarpathia. <http://www.soniachna-dolina.com/en/treatment_2.html> (Accessed on Sep. 22, 2011) (2 pages).

Benner, R.W., and Drake, J.W., "IV Therapy for EMS," Chapter 3. Pearson Prentice Hall. <http://bit.ly/q12yxc> (2006). pp. 20-31.

Schmidt, "Redox Homeostasis and Microbial Colonisation of Wounds: New Insights into the Energy Economy of Chronic Wounds," Journal für Anästhesie und Intensivbehandlung. vol. 3, No. 3, pp. 26-31 (1996).

Toledo, T.K., and DiPalma, J.A., "Review article: colon cleansing preparation for gastrointestinal procedures," Alimentary Pharmacology & Therapeutics. vol. 15 pp. 605-611 (2001).

* cited by examiner

Effect on human dermal fibroblast (12 year old donor, 5th passage) metabolism of 4-hour exposure to various saline : DMEM / 10% FCS (1 : 1) solutions as measured by the MTT assay immediately after exposure and after a 43-hour recovery period in DMEM / 10% FCS ATP content of 161BR human skin-derived fibroblasts following exposure to various NaK saline : K-free EMEM (1 : 1) solutions for increasing periods of time as measured by the ViaLight™ bioluminescence assay \* Significantly greater than
NaK saline5 ( p=0.05 )

ATP content of 161BR human skin-derived fibroblasts following exposure to various saline : K-free EMEM (1 : 1) solutions for increasing periods of time as measured by the ViaLight™ bioluminescence assay

** Significantly greater than both
   Normal saline ( p=0.0002 ) and
   Ringer solution ( p=0.004 )
* Significantly greater than both
   Normal saline ( p=0.00000001 ) and
   Ringer solution ( p=0.03 )

SALINE SOLUTIONS FOR CLINICAL OR COSMETIC USE

This invention relates to a saline solution for clinical or cosmetic purposes, for use, for example, as an irrigation solution for body surfaces or body cavities, as a nebuliser solution, as a wetting solution in the preparation of wet dressings for application to chronic skin ulcers, as a pharmaceutical vehicle, or as a blood volume expander following severe hemorrhage.

Traditionally, saline solution for these purposes has consisted essentially of sodium chloride dissolved in water. Typically, such a solution of sodium chloride in water is prepared in accordance with an appropriate pharmacopoeial monograph. Examples of such preparations include Sodium Chloride Solution prepared in accordance with the British Pharmacopoeia, and Sodium Chloride Irrigation prepared in accordance with the United States Pharmacopoeia. Such saline solution prepared in accordance with an appropriate pharmacopoeial monograph is commonly known as "normal saline" when it is prepared to contain 0.9% of sodium chloride on a weight in volume basis. For the avoidance of ambiguity here and hereinafter, this should be understood as indicating the dissolution of 0.9 grams sodium chloride in water sufficient to produce a final volume of 100 milliliters. Other definitions expressed herein on a percentage weight/final volume basis also denote grams of a salt/100 ml final volume.

It should be noted that primary pharmacopoeias, for example the British Pharmacopoeia or the European Pharmacopoeia, provide monographs describing minimum quality standards for named substances or preparations. Compliance of a preparation with a standard given in a named pharmacopoeial monograph helps ensure consistency of quality between batches and suppliers. Normally, no reference is made to the uses of named substances or preparations although appropriate doses may be given. In contrast, secondary pharmacopoeias, for example Martindale's Extra Pharmacopoeia, provide more detailed monographs of substances or preparations, which may include uses, toxic effects, and contraindications but which do not normally include quality standards except insofar as reference will be given to an appropriate primary pharmacopoeia in which a quality standard is to be found.

Secondary pharmacopoeias published in the early 1900s, for example on page 722 in volume 1 of the $16^{th}$ edition of W H Martindale & W W Westcott's The Extra Pharmacopoeia published in 1915 by H K Lewis & Company, London, reveal that normal saline solution was originally developed for use by intravenous injection as a blood volume expander in the treatment of surgical shock following severe blood loss. In order to avoid lysis of red blood cells, the importance of using a solution having the same osmotic pressure as blood plasma was recognised. Hence a solution containing 0.9% sodium chloride in water on a weight in volume basis, being isotonic with blood plasma, became known as "normal saline solution" or "physiological salt solution".

Isotonic or iso-osmotic solutions are solutions that exert the same osmotic pressure when separated by a semi-permeable membrane and therefore there is no movement of solvent across the membrane. When the semi-permeable membrane is a mammalian cell wall, for example a cell wall of a red blood cell, a solution that is iso-osmotic with blood will cause the red blood cell to neither swell nor shrink. In contrast, a solution that exerts a greater osmotic pressure than blood plasma will cause red blood cells to exude water and hence to shrink. This is usually reversible. A solution that exerts a lower osmotic pressure than blood plasma will cause red blood cells to take in water and hence to swell and eventually burst. The process of cell bursting, otherwise known as cell lysis, is irreversible. A fuller description of isotonic and iso-osmotic solutions is set out on page 219 in the $18^{th}$ edition of the Pharmaceutical Handbook (edited by R G Todd) published in 1970 by the Pharmaceutical Press, London.

The present invention involves the replacement of some of the sodium ions in normal saline solution with a defined quantity of potassium ions as it has been found that this leads to a saline solution with enhanced properties as described below.

Nevertheless, the uses to which the solutions of the present invention may be put encompass all those uses to which normal saline is currently put when it is brought into direct and primary contact with an external or internal surface of a living human or animal tissue or organ, and including the use for which it was originally developed, namely use as a blood volume expander. Thus, normal saline is used both as a vehicle and as a diluent for nebuliser and respirator solutions formulated to facilitate the administration of substances, for example salbutamol sulfate and ipratropium bromide, to the lungs by means of inhalation. Normal saline is also used as a vehicle or diluent for injections or infusions formulated to deliver a wide variety of therapeutic or diagnostic agents subcutaneously, intradermally, Intravenously, intramuscularly, intrathecally, or by other routes. Furthermore, it is used as a vehicle for eye drops, nose drops and for other such pharmaceutical presentations designed to deliver therapeutic or diagnostic substances to body surfaces and body cavities. Normal saline is also in widespread use as an irrigant for cleansing internal or external body surfaces and body cavities, for example the skin, the eyes, and the bladder. It is also used, soaked onto gauze or alternative substrates as a dressing for burns, chronic skin ulcers and other wounds. These and other uses in clinical and cosmetic practice will be evident to skilled practitioners, as will uses in veterinary medical practice. The solutions of the present invention can beneficially replace normal saline in all of the above mentioned uses.

Further uses to which normal saline and therefore also the solutions of the present invention may be put include those in which the saline solution is brought into direct and primary contact with a medical or cosmetic device. Examples of such further uses include uses calculated to wet, rinse, cleanse, preserve, or facilitate transport or storage of said medical or cosmetic devices. Examples of said medical or cosmetic devices include hard, soft and disposable contact lenses. Examples of said medical devices also include urethral urinary catheters.

Normal saline solution is to be distinguished from more complex saline solutions formulated for the purpose of making use of the properties of calcium, magnesium, phosphate, and/or bicarbonate ions. Whilst uses of such saline solutions may encompass uses to which normal saline is currently put, the saline solutions of the present invention exert their beneficial effect without the need to add calcium, magnesium, phosphate, and/or bicarbonate ions.

Normal saline solution is also to be distinguished from saline solutions that are formulated to contain glucose and glucose-releasing saccharides such as sucrose or food starch that enhance sodium ion and water uptake during oral rehydration therapy. In this use, normal saline prepared in accordance with an appropriate pharmacopoeial monograph for Sodium Chloride Irrigation or Sodium Chloride Solution cannot be used as a substitute and therefore neither can the saline solutions of the present invention.

Normal saline solution is further to be distinguished from saline solutions formulated to contain sodium chloride and potassium chloride in water for injections, with or without additional ingredients, and intended for intravenous infusion for the purpose of correcting electrolyte imbalance. In this use, normal saline prepared in accordance with an appropriate pharmacopoeial monograph for Sodium Chloride Infusion again cannot be used as a substitute. It follows that both Sodium and Potassium Chloride Infusion prepared in accordance with an appropriate pharmacopoeial monograph, and any other pharmacopoeial or proprietary product formulated for the purpose of correcting electrolyte imbalance by intravenous infusion falls outside the scope of this patent specification.

For some of the above-listed uses of normal saline, some practitioners prefer to use tap water as a less costly substitute. In 1998, R M Moscati and co-authors published two articles describing the results of their studies using tap water for wound irrigation. The first, entitled "Wound irrigation with tap water", was published on pages 1076-1080 in volume 5 of Academic Emergency Medicine. The second, entitled "Comparison of normal saline with tap water for wound irrigation", was published on pages 379-381 in volume 16 of the American Journal of Emergency Medicine. Earlier, in 1992, M Hall Angeras and co-authors published details of a similar study on pages 347-350 in volume 158 of the European Journal of Surgery in an article entitled "Comparison between sterile saline and tap water for the cleaning of acute traumatic soft tissue wounds". In these studies, outcomes were compared following the use of either tap water or normal saline for Irrigation of simple traumatic wounds and lacerations in hospital emergency departments. Rates of healing were assessed in terms of infection rates. Infection rates were found not to increase following irrigation with tap water. Although these studies were not done in patients with chronic skin ulcers, tap water has subsequently been promoted as a cheap alternative to normal saline for the simple irrigation of chronic ulcers. It should be noted that tap water usually contains adventitious calcium and magnesium ions.

Where tap water is promoted for use as an inexpensive substitute for normal saline, no reference is made to the fact that tap water, because it is extremely hypotonic, can cause irreversible cell lysis after a short period of time. The effect of hypotonic solutions on blood cells is discussed in more detail in the aforementioned Pharmaceutical Handbook, whilst J L Jay & M MacDonald in 1978 on pages 815-820 in volume 62 of the British Journal of Ophthalmology, in an article entitled "Effects of intraocular miotics on cultured bovine endothelium", describe the damaging effect on bovine endothelial cells of just 5 minutes exposure to tap water.

Another alternative to normal saline favoured by practitioners in certain countries is Ringer solution. Sydney Ringer developed his Ringer solution in the 1880s as a physiological saline solution that supports the beating and rhythmicity of isolated frog heart preparations. This solution contains sodium bicarbonate in addition to sodium, potassium, and calcium chlorides. Since that time, numerous variations of Ringer's original formulation have been developed by those studying vertebrate and invertebrate physiology. Now, the term Ringer solution is used loosely to describe almost any "physiological saline solution" used by biologists. A variety of additional ingredients such as magnesium chloride and sodium acid phosphate may be included depending upon the field of use. At least one such Ringer solution is currently available as a commercial product for clinical use as an irrigation solution, namely Hartmann Ringer Solution marketed in the UK by Paul Hartmann Limited. This solution contains only sodium, potassium and calcium chlorides in water and is essentially identical in composition to Compound Sodium Chloride Injection described in the British Pharmaceutical Codex of 1959 and Ringer's Irrigation described in the United States Pharmacopoeia. However, the present invention provides a saline solution of greater simplicity, which is therefore cheaper to produce and which, as described in Example 2 below, has advantages over both Hartmann Ringer solution and the traditional or normal saline solution which consists essentially of an isotonic solution of sodium chloride in water.

For some of the above-listed uses of normal saline, solutions of sodium chloride containing additives, for example antimicrobials, antioxidants, or surfactants, are preferred by some practitioners. Normal saline-based irrigation solutions containing antimicrobials, antioxidants, and/or surfactants are more expensive to produce than normal saline alone and have been found to exert greater or lesser degrees of cytostatic or cytotoxic activity in cell culture-based assays. Reports of such cytostatic or cytotoxic activity have been published by, amongst others, S S Brennan and co-authors, in the Journal of Hospital Infection, volume 8, pages 263-267, 1986 (in an article entitled "Antiseptic toxicity in wounds healing by secondary intention"); M L Cooper and co-authors in the Journal of Trauma, volume 31, pages 775-784, 1991 (in an article entitled "The cytotoxic effects of commonly used topical antimicrobial agents on human fibroblasts and keratinocytes"); P A Foresman and co-authors in Wounds, volume 5, pages 226-231, 1993 (in an article entitled "A relative toxicity index for wound cleansers"); and T B Hellewell and co-authors in Wounds, volume 9, pages 14-19, 1997 (in an article entitled "A cytotoxicity evaluation of antimicrobial and non-antimicrobial wound cleansers"). However, the incorporation of additives such as antimicrobials, antioxidants and surfactants into the solutions of the present invention is not precluded for those necessary additives, for example antimicrobials or antioxidants required to ensure safety in use and stability of the solution when packaged in multi-use re-closable containers, said necessary additives being characterised in that no loss of the advantage for cell function of the solution of the invention occurs when the solution is evaluated using the methods described hereunder in Examples 1 & 2.

It has previously been considered that normal saline, because it is isoosmotic with blood plasma, neither stimulates nor depresses function of cells with which it is brought into contact. However, it is known, but not widely appreciated, that normal saline is itself damaging to mammalian tissues. Thus, R D Acland and co-authors in Plastic and Reconstructive Surgery, volume 65, pages 460-465, 1980 (in an article entitled "Irrigating solutions for small blood vessel surgery—a histologic comparison") used a variety of histological parameters to assess the damaging effects of five irrigating solutions suspected to cause tissue damage when used during microvascular surgery. The irrigation solutions studied were normal saline, lactated Ringer solution, Normosol R pH 6.2, Normosol R pH 7.4, and glutathione-buffered Ringer solution. The authors of the study reported that, of these five Irrigation solutions, normal saline consistently produced the most severe damage to endothelial cells in 1-mm rat femoral arteries, but did not venture to suggest why this might be the case. More recently, T Wang and co-authors in the International Journal of Artificial Organs, volume 22, pages 88-93, 1999 (in an article entitled "Physiological saline is not a biocompatible peritoneal dialysis solution") described a study of the biocompatibility of normal saline in the context of its use as a peritoneal dialysis solution. Their study was carried out in rats. The conclusion they reached, which was based on their observation of increased peritoneal lymphatic flow and an increase in radio-labeled human albumin uptake, was that normal saline is not a biocompatible peritoneal dialysis solution. These authors noted that the most commonly cited parameters of peritoneal dialysis solutions that are considered to be bio-Incompatible are glucose, glucose degradation products, calcium, high osmolality, low pH, and high lactate content. However, as a result of their study and of their evaluation of the results of earlier published studies, they discounted all of these parameters, suggesting instead that the outcomes they observed might be due simply to a physiological adaptation to the unnaturally high level of fluid to which the peritoneal membranes were exposed.

Surprisingly, it would now appear from our studies that normal saline can itself depress cell function and, furthermore, that this inhibitory effect can be reduced or eliminated simply by the replacement of some of the sodium chloride with a specific amount of potassium chloride, or optionally an alternative source of potassium ions thereby producing a preparation containing in its simplest embodiment only sodium, chloride, and potassium ions. Such formulations, when made to be iso-osmotic with blood plasma, display significantly enhanced biocompatibility when compared with tap water, normal saline, or more complex saline-based solutions. The saline solutions herein disclosed also offer a cost advantage over Ringer solution and other more complex saline-based irrigation solutions.

Thus, the saline preparations of this invention consist essentially of sodium ions in a major amount and potassium ions in a lesser, and specific, amount in a physiologically or cosmetically acceptable aqueous solvent, the source or sources of potassium and sodium ions providing physiologically compatible counter ions.

In order to distinguish the saline solutions of this invention from more complex solutions described in the prior art and from solutions containing sodium and chloride ions but not intended for clinical or cosmetic purposes, the saline solutions of this invention are hereby specified as being substantially free of calcium, magnesium, phosphate, and bicarbonate ions. To distinguish the saline solutions of this invention from formulations intended for oral rehydration therapy, they are also specified as being substantially free from glucose and glucose-releasing saccharides such as sucrose or food starch.

Thus, the present invention provides saline preparations for a clinical or cosmetic purpose requiring direct and primary contact of the saline preparation with an external or internal surface of a living human or animal tissue or organ, or direct and primary contact with a medical or cosmetic device, said clinical or cosmetic purpose having hitherto been fulfilled by a solution known commonly as normal saline comprising a solution of sodium chloride in water. The saline preparations of the present invention consist essentially of a solution in potable or purified water of sodium ions in an amount corresponding to an amount of sodium chloride within the range 0.6% to 0.9% weight by volume, characterised in that the solution also contains potassium ions in an amount corresponding to an amount of potassium chloride within the range 0.001% to 0.3% weight by volume, the preparation being in the range of 80 to 120 percent of the osmotic activity of blood plasma or tears or of an otherwise relevant body fluid measured in milliosmols and being substantially free of calcium ions, magnesium ions, phosphate ions, bicarbonate ions and glucose, sucrose, food starch or other glucose-releasing saccharides.

Preferably, the source of sodium ions is sodium chloride and the source of potassium ions is potassium chloride. The preferred solvent is water. Alternative sources of sodium and potassium ions together with physiologically compatible counter ions will be evident to the skilled reader, as will alternative aqueous solvents.

Alternative aqueous solvents may include water in which one or more substances, for example mannitol or hydroxypropyl methylcellulose, have been incorporated as tonicity or viscosity adjusting agents.

Preferably, the quantities of sodium chloride, potassium chloride, and water are chosen to produce a solution that falls in a range of 95 to 105% of the osmotic activity of blood plasma, measured in milliosmols, and most preferably, the quantities of sodium chloride, potassium chloride, and water are chosen to produce a solution that is iso-osmotic with blood plasma or tears.

Preferably, the final concentration of sodium chloride in the solution falls in the range 0.78% to 0.88% weight by volume, and is most preferably 0.86% weight by volume. Preferably, the final concentration of potassium chloride falls in the range 0.01% to 0.15% weight by volume, more preferably 0.015% to 0.15% weight by volume, and is most preferably 0.015% weight by volume, the relative amounts of sodium and potassium chlorides being chosen so that the solution falls within the aforementioned range of osmotic activity and preferably within the aforementioned preferred range of osmotic activity, with it being most preferred that the solution is iso-osmotic with blood plasma or tears.

Osmotic activity may be determined by a variety of means, these including experimental methods and methods involving theoretical calculations. The precise result obtained depends on the method used. For the purpose of specification of the saline solutions of this invention, two calculation methods are used, the first relating milliosmols to milliequivaients for determining the preferred and more preferred ranges, the second and more accurate method based on depression of freezing point calculations for determining the most preferred compositions of this invention.

One milliosmol is taken as being the osmotic activity of one milliequivaient of solute. For dilute solutions of completely dissociated monovalent electrolytes such as sodium chloride and potassium chloride, one milliequivaient is the atomic/molecular weight in milligrams of each ionic species present in each liter of the final solution.

Thus, the number of milliequivaients (and hence osmotic activity in milliosmols) of any chosen quantities of sodium chloride and potassium chloride may be calculated using the following relationship:

$$([NaCl\ mg\ per\ liter] \times 2/58.44) + ([KCl\ mg\ per\ liter] \times 2/74.55)$$

Although such calculation reveals that iso-osmotic solutions of sodium and potassium chlorides as determined using the method based on depression of freezing point calculations contain 308 to 319 milliequivaients, practitioners skilled in the art will be aware that for practical purposes, a solution having an osmotic activity of 300 milliosmols is considered to be iso-osmotic with blood plasma.

Accordingly, the quantities of sodium chloride, potassium chloride and water required to produce saline solutions of this invention are chosen to produce saline solutions having a calculated osmotic activity falling in the range 240 to 360 milliosmols, and preferably in the range 285 to 315 milliosmols. For the most preferred saline solutions of this invention, quantities of sodium chloride, potassium chloride and water are calculated using the method based on depression of freezing points as described in Example 1 below.

The solutions described in this invention may be used for all clinical or cosmetic purposes for which normal saline might be used. The solutions may be packaged in any suitable container made of any suitable material, for example glass, plastic, or metal bottles, bags, ampoules, aerosols, blow fill seal (also called form fill seal) containers, and sachets. It will be evident to skilled practitioners that the solutions may require sterilisation by a suitable means prior to use in certain applications.

The solutions may also be incorporated into carrier substrates, for example hydrogels, hydrocolloids, sponges, foams, gauzes, bandages, pastes, and plasters for application to internal or external body surfaces. Said carrier substrates may confer additional beneficial properties, for example absorbency, adsorbancy, gas and moisture vapour permeability, odour control, and antioxidant activity.

If desired or necessary, the solutions of the invention may include minor amounts of one or more physiologically acceptable antimicrobial agents, surfactants, antioxidants, colouring, or aromatizing agents where such addition does not lead to a demonstrable loss of the advantage for cell function of the solutions of the invention over normal saline when assessed using the methods described in Examples 1 and 2 below.

If required for the purpose of ensuring the stability or activity of dissolved or suspended medicaments, the solutions of the invention may also include pH buffering agents where such addition does not lead to a demonstrable loss of the advantage for cell function of the solutions of the invention over normal saline. Preferably, however, the preparation does not contain pH-buffering agents.

If further desired, the solutions of the invention either alone or after incorporation in a carrier substrate, may be warmed to enhance activity. Said warming may be applied prior to and during use.

Uses of saline preparations of the present invention constitute further aspects of the present invention. One example is the cleansing of wounds or burns.

Another example is the cleansing of body surfaces.
Another example is the cleansing of body cavities.
Another example is the dressing of wounds or ulcers after absorption onto a suitable substrate.
Another example is the administration of medicaments to the ears, eyes, or nose.
Another example is the administration of medicaments to the lungs by nebulisation.
Another example is the administration of medicaments or diagnostic agents by Injection or Infusion.
Another example is the expansion of blood volume by intravenous infusion.
Another example is peritoneal dialysis.
Another example is as a transport or storage solution for contact lenses.
Another example is as a wetting or rinsing solution for contact lenses.
Another example is as a catheter maintenance solution.
Another example is as a general cleansing, rinsing and storage solution for maintaining medical devices.

Figure 1:
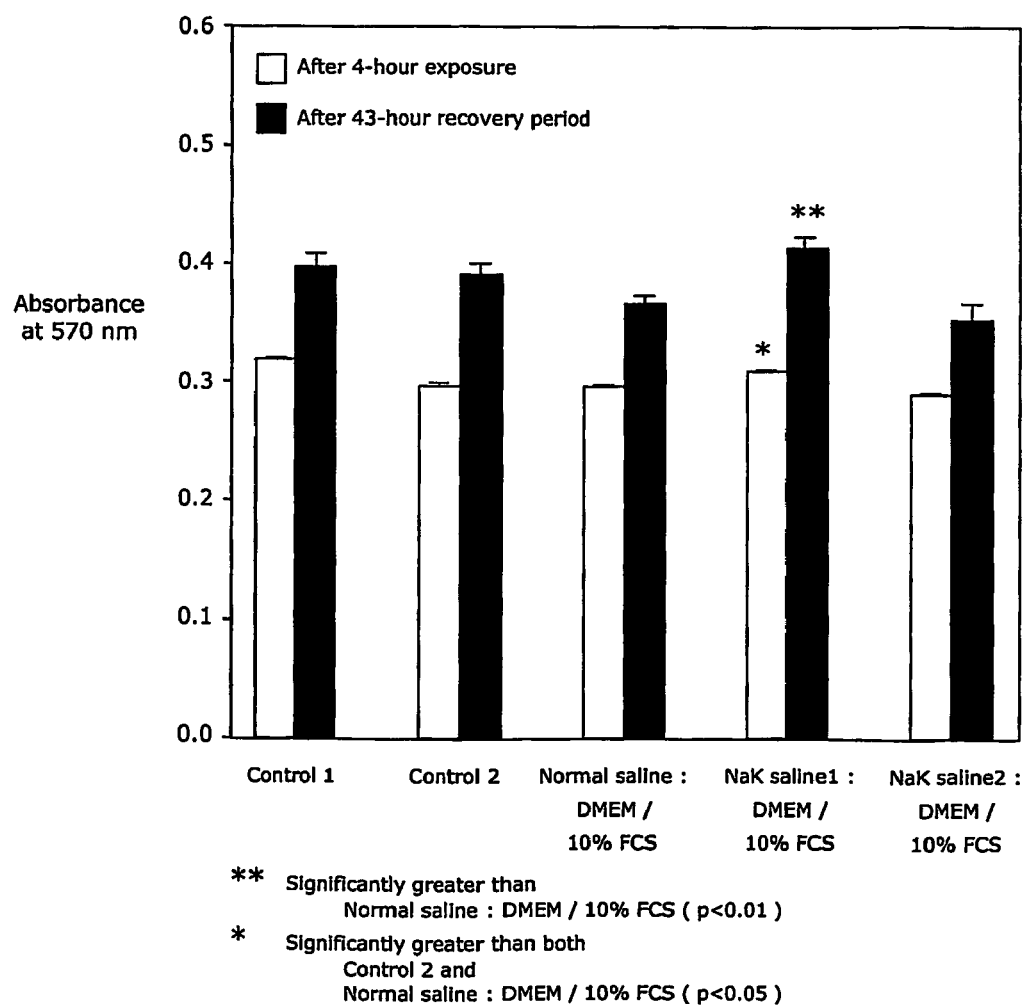
FIGS. 1-3 depict the effect of the instant saline solution with NaCl and KCl on fibroblasts compared to conventional saline solutions.

The effects of the saline solutions of the present invention are illustrated by the following non-limiting Examples

EXAMPLE 1

Saline solutions were prepared by dissolving quantities of sodium chloride (NaCl) and potassium chloride (KCl) in purified water as specified In Table 1:

TABLE 1

| Saline solutions prepared to contain in 100 ml: | | | |
|---|---|---|---|
| Designation: | Normal saline | NaK saline1 | NaK saline2 |
| NaCl | 0.90 g | 0.78 g | 0.72 g |
| KCl | | 0.16 g | 0.24 g |

Quantities of sodium chloride and potassium chloride were calculated according to the following relationship in accordance with the method described on page 219 in the 18$^{th}$ edition of the Pharmaceutical Handbook published in 1970 by the Pharmaceutical Press, London, to produce solutions that are isotonic with blood plasma:

$KCl = (0.52 - 0.576 \cdot NaCl)/0.439$ g per 100 ml

Fibroblasts (5$^{th}$ passage) from a 12 year old human donor were seeded in two 96-well plates in 100 µl of Dulbecco's Modified Eagle's Medium (DMEM)/10% foetal calf serum (FCS) at $2 \times 10^4$ cells/well. Before testing, cells were grown to confluence in a humidified incubator (5% $CO_2$/95% air atmosphere) at 37° C. For the assays, medium was removed by aspiration from the wells to be used for test saline solutions and from wells to be used for control 2. For control 2, medium was replaced with fresh DMEM/10% FCS. Medium was not removed from wells to be used as control 1. In test wells, medium was replaced with a 1:1 mixture of fresh DMEM/10% FCS:saline solution. Plates were then returned to the incubator. After 4 hours, plates were removed from the incubator. Control 1 wells were left undisturbed whilst medium was again removed by aspiration from test wells and from control 2 wells and replaced with fresh DMEM/10% FCS (100 µl). The MTT assay was then performed on one of the plates; the other was returned to the incubator for a further 43 hours before also being subjected to the MTT assay.

The MTT assay was performed using the method described in 1989 by M B Hansen, S E Nielsen & K Berg on pages 203-210 in volume 119 of the Journal of Immunological Methods in their article entitled "Re-examination and further development of a precise and rapid dye method for measuring cell growth/cell kill". The yellow M17 [3-(4,5-dimethylthiazol-2-yl)-2,5-diphenyl-tetrazolium bromide] solution is reduced by living cells to a blue formazan, which can be solubilised, eluted and measured in a spectrophotometer. MTT solution (5 mg/ml in phosphate buffered saline; 25 µl) was added to the medium In each well. After 2-hours incubation at 37° C., medium was removed and 100 µl of acidified sodium dodecyl sulfate in dimethylformamide/water (1:1 v/v) at pH 4.3 was added to each well to solubilize the blue formazan. Absorbance was then measured at 570 nm, using solvent as blank, In a Dynatech NRX microplate reader.

Multiple analyses of variance were carried out by one way analysis of variance (ANOVA) for the data at each time point. Where significant F values were obtained using ANOVA, Fisher's PLSD procedure was used to determine significant differences (p<0.05) between the means of absorbance values under different treatments. Sets of 6 or 7 wells were used for each test solution and for controls. Outlier values were not rejected.

Results are presented in FIG. 1. It is evident that metabolic activity in test wells exposed to normal saline was depressed relative to control 2 after the 43-hour recovery period (p=0.15). It is evident also that metabolic activity in test wells exposed to NaK saline1 was elevated relative to control 2 (p=0.18) and even more so relative to normal saline (p=0.007). This elevation of metabolic activity with NaK saline1 relative to both control 2 (p=0.03) and normal saline (p=0.03) was already evident Immediately after the 4-hour period of exposure. NaK saline2 exposure, in contrast, led to a depression of metabolic activity relative to control 2 after the 43-hour recovery period (p=0.02).

It will be evident to those skilled in the art that stimulation of metabolic activity in the shorter or in the longer term Is a desirable outcome in many circumstances where normal saline is currently in use, for example during irrigation of chronic ulcers at dressing change or Irrigation of eyes following trauma.

EXAMPLE 2

Saline solutions were prepared by dissolving quantities of sodium chloride (NaCl), potassium chloride (KCl), and calcium chloride ($CaCl_2.2H_2O$) in purified water as specified in Table 2:

TABLE 2

Saline solutions prepared to contain in 100 ml:

| Designation: | Normal saline | NaK saline3 | NaK saline4 | NaK saline5 | Ringer soln |
|---|---|---|---|---|---|
| NaCl | 0.903 g | 0.891 g | 0.880 g | 0.868 g | 0.860 g |
| KCl | | 0.015 g | 0.030 g | 0.045 g | 0.030 g |
| $CaCl_2.2H_2O$ | | | | | 0.033 g |

Quantities of sodium chloride and potassium chloride for NaK saline3, NaK saline4, and NaK saline5 were calculated according to the following relationship in accordance with the method described on page 219 in the $18^{th}$ edition of the Pharmaceutical Handbook published In 1970 by the Pharmaceutical Press, London, to produce solutions that are isotonic with blood plasma:

$$KCl=(0.52-0.576.NaCl)/0.439 \text{ g per } 100 \text{ } ml$$

Quantities of sodium chloride, potassium chloride and calcium chloride for Ringer solution are as provided in the monograph for Compound Sodium Chloride Injection of the British Pharmaceutical Codex 1959.

A 4 ml cell suspension of 161BR human skin-derived fibroblasts was made by harvesting cells from four confluent T175 flasks, and re-suspending them in fresh EMEM containing 15% serum. Cell numbers were assessed by haemocytometer counting.

After thoroughly suspending cells, a diluted cell suspension was then prepared in a Universal tube such that 100 µl contained 5,000 cells. This suspension was poured into a sterile tray and the cells pipetted into the wells (5000/well) of rows b to f of each 96-well plate, one column at a time using a Jencons 8-channel pipette. The tray was agitated between each pipetting. Pipette tips were not changed between each pipetting, and tips were exposed to cell suspension (by repeat pipetting) before seeding of first column of plate began. Care was taken to avoid bubble formation as each aliquot was added. The suspension was pipetted to bottom centre of wells. Four plates were prepared identically. No cells were seeded in the top and bottom two rows. Instead, 100 µl sterile phosphate buffered saline (PBS) was added to each of these wells. Plates were left at room temperature in a laminar flow cabinet for one hour and then thoroughly wrapped in "cling film" before being placed in a humidified plastic box with the lid slightly ajar and incubated at 37° C. in a 5% $CO_2$ atmosphere overnight.

Various saline formulations (see Table 2 above) were mixed in 1:1 ratio with Eagle's Minimum Essential Medium (EMEM) containing no KCl, antibiotics or serum. These saline/culture medium mixtures were then transferred to template 96-well plates. Overnight culture medium (EMEM containing 15% serum) was then removed from each of the test plates in turn and replaced by the saline/culture medium mixtures in the template plates using a Jencons multichannel pipette. Treatments were added down rows rather than across columns to reduce the number of times it was necessary to change tips. Plates (except plate 1, which was to be assayed immediately) were re-wrapped in cling film and returned to the incubator in humidified boxes.

ViaLight™ assays (kit obtained from LumiTech Ltd, Nottingham, UK) were carried out on plates 1, 2, 3 and 4 at 0 h, 2 h, 4 h and 6 h respectively. Medium was removed from the cells in each well and 100 µl of reconstituted nucleotide releasing reagent (NRR) was added immediately to each well. After 10 minutes at room temperature to allow extraction, plates were transferred to a Lucy-2 luminometer. The automated injection system of the Lucy-2 was used to add 50 µl of nucleotide monitoring reagent (NMR) to each well, then 1-second integrated readings were immediately initiated for each well.

The ViaLight™ assay provides a means by which the ATP content of living cells can be measured using bioluminescence.

Studies using filter-sterilised tap water in place of saline were also performed. The resulting 1:1 water/culture medium mixtures were hypotonic. As mentioned above, hypotonic solutions are known to cause cell swelling and, if severe, cell lysis. This property rendered results generated by the ViaLight™ assay invalid because of the additive effect of hypotonicity and the nucleotide releasing reagent (NRR) on the release of ATP from cells prior to quantification using the nucleotide monitoring reagent (NMR). Therefore, results from these studies were ignored.

Figure 2:
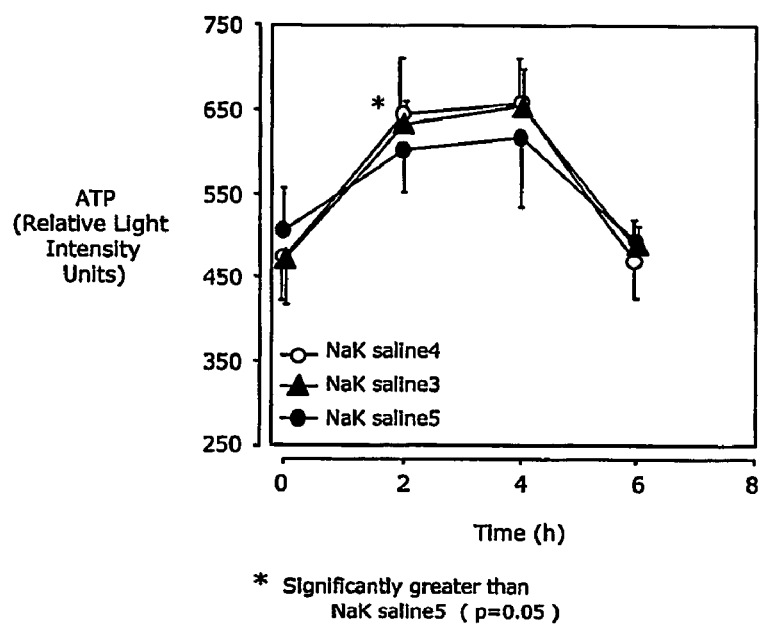
Figure 3:
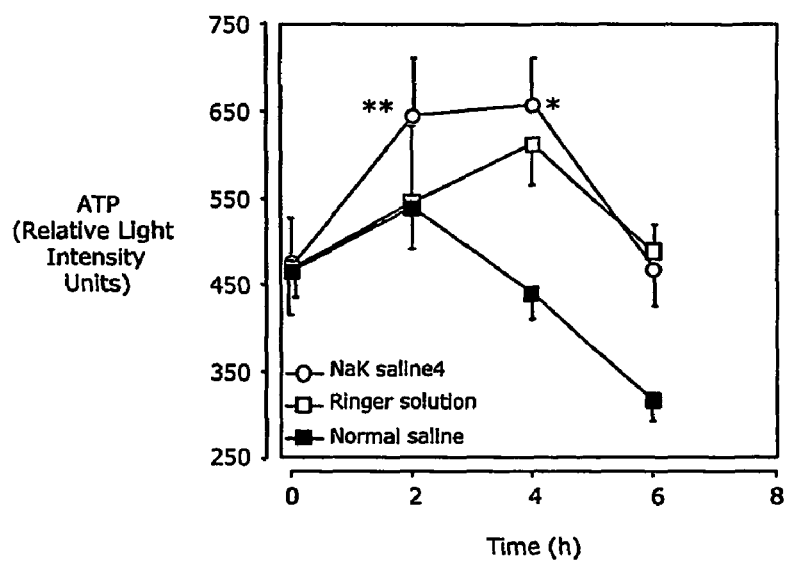

Results from the five saline solutions tested are presented in FIGS. 2 and 3. It is evident that ATP content of 161BR human skin-derived fibroblasts exposed to a 1:1 mixture of normal saline with KCl-free EMEM is markedly lower at all time points than that seen with mixtures of KCl-free EMEM with NaK saline3, NaK saline4 or NaK saline5. ATP content of cells exposed similarly to Ringer solution were intermediate between those seen with normal saline and those seen with NaK saline3, NaK saline4 & NaK saline5.

Statistical analysis revealed highly significant differences between ATP levels in 161BR fibroblasts exposed to normal saline and the NaK saline solutions of the present invention:

At all time points after t=0 h, all three NaK saline solutions produced ATP values that were significantly greater than those produced with normal saline. Student's t-test generated p values ranging from 0.0042 to 0.000000000004. These data demonstrate that the biocompatibility of normal saline is severely compromised by the absence of potassium ions.

At t=2 h, all three NaK saline solutions produced ATP values that were significantly greater than those produced with Ringer solution (p values ranging from 0.046 to 0.0041).

At t=4 h, NaK saline3 and NaK saline4 but not NaK saline5 produced ATP values that were significantly greater than those produced with Ringer solution (p values 0.031 & 0.034).

At t=6 h, there was no significant difference between NaK saline3, NaK saline4, & NaK saline5 and Ringer solution. As ATP levels were all waning, cell cultures were evidently degenerating. Therefore, It is probably inappropriate to attempt to extrapolate these findings at t=6 h to a clinical situation.

NaK saline4 produced the highest ATP levels at t=2 h. However, when extrapolating from the formulation of NaK saline4 to the most preferred content of sodium and potassium ions for the solutions of the present invention, it is necessary to take into account the final content of sodium and potassium ions in the saline/culture medium mixture to which the fibroblasts were exposed. Surprisingly, a final concentration of potassium ions of about 2 mM (corresponding to a concentration of KCl of about 0.015 g per 100 ml) was found to be optimal, a concentration below that normally present in either human plasma or EMEM of standard composition.

It will be evident to those skilled in the art that increased availability of ATP within cells in the shorter or in the longer term is a desirable outcome in many circumstances where normal saline is currently in use, for example during irrigation of chronic ulcers at dressing change or irrigation of eyes following trauma.

The invention claimed is:

1. A method of cleansing or dressing a wound, burn or ulcer on a skin surface or of irrigating a skin surface, comprising:
   a) preparing a saline preparation consisting essentially of a solution in water of sodium ions within the range 0.283% to 0.346% weight by volume, wherein the solution also contains potassium ions within the range 0.001% to 0.1257% weight by volume, the preparation having an osmotic activity within the range of 240 to 360 milliosmols and the source of sodium ions is sodium chloride and the source of potassium ions is potassium chloride; wherein the saline preparation is free of calcium ions, magnesium ions, phosphate ions, bicarbonate ions, glucose, sucrose, and food starch; and
   b) directly contacting the skin surface with the saline preparation or contacting the skin surface with a carrier substrate in which said saline preparation has been incorporated.

2. A method according to claim 1 wherein the osmotic activity is within the range 285 to 315 milliosmols.

3. The method of claim 1, wherein the sodium ions are within the range of 0.306% to 0.346% weight by volume.

4. The method of claim 1, wherein the sodium ions are at a concentration of 0.338% weight by volume.

5. The method of claim 1, wherein the carrier substrate is selected from the group consisting of sponges, foams, gauzes, bandages, pastes, and plasters.

* * * * *

UNITED STATES PATENT AND TRADEMARK OFFICE
CERTIFICATE OF CORRECTION

| | |
|---|---|
| PATENT NO. | : 8,236,863 B2 |
| APPLICATION NO. | : 10/490811 |
| DATED | : August 7, 2012 |
| INVENTOR(S) | : Schmidt et al. |

It is certified that error appears in the above-identified patent and that said Letters Patent is hereby corrected as shown below:

On title page, item 75 Inventors
replace "Barnoldswick (GB)"
with --Penarth (GB)--.

On title page, item 75 Inventors
replace "Godalming (GB)"
with --Shawnee, OK (US)--.

On title page, item 73 Assignee
replace "Goldalming, Surrey (GB)"
with --Shawnee, OK (US)--.

Signed and Sealed this
Sixteenth Day of October, 2012

David J. Kappos
*Director of the United States Patent and Trademark Office*